United States Patent
Wall et al.

(10) Patent No.: US 10,448,978 B2
(45) Date of Patent: Oct. 22, 2019

(54) SPINAL IMPLANT SYSTEM AND METHOD

(71) Applicant: Warsaw Orthopedic, Inc., Warsaw, IN (US)

(72) Inventors: Daniel Paxton Wall, Cordova, TN (US); Adam Glaser, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 6 days.

(21) Appl. No.: 15/661,986

(22) Filed: Jul. 27, 2017

(65) Prior Publication Data

US 2019/0029737 A1   Jan. 31, 2019

(51) Int. Cl.
| | |
|---|---|
| A61B 17/70 | (2006.01) |
| A61B 17/86 | (2006.01) |
| A61B 17/88 | (2006.01) |
| A61B 90/00 | (2016.01) |
| A61B 34/20 | (2016.01) |

(52) U.S. Cl.
CPC .......... *A61B 17/7082* (2013.01); *A61B 17/86* (2013.01); *A61B 17/8886* (2013.01); *A61B 17/7035* (2013.01); *A61B 34/20* (2016.02); *A61B 90/39* (2016.02)

(58) Field of Classification Search
CPC ........................................ A61B 17/7074–7082
See application file for complete search history.

(56) References Cited

U.S. PATENT DOCUMENTS

| | | | |
|---|---|---|---|
| 2,691,979 A | 10/1954 | Watson | |
| 5,390,383 A | 2/1995 | Carn | |
| 6,021,343 A * | 2/2000 | Foley | A61B 17/16 600/417 |
| 7,189,214 B1 | 3/2007 | Saunders | |
| 7,234,180 B2 | 6/2007 | Horton et al. | |
| 7,290,302 B2 | 11/2007 | Sharps | |
| 7,496,980 B2 | 3/2009 | Sharps | |
| 8,784,431 B1 * | 7/2014 | Harder | A61B 17/7082 606/104 |
| 9,192,415 B1 * | 11/2015 | Arnold | A61B 17/7082 |
| 2003/0023243 A1 * | 1/2003 | Biedermann | A61B 17/7032 606/308 |
| 2005/0228400 A1 * | 10/2005 | Chao | A61B 17/7082 606/104 |
| 2007/0043378 A1 * | 2/2007 | Kumar | A61B 17/7082 606/104 |
| 2008/0045970 A1 * | 2/2008 | Saidha | A61B 17/7032 606/104 |

(Continued)

FOREIGN PATENT DOCUMENTS

| | | |
|---|---|---|
| WO | 2007058673 A1 | 5/2007 |
| WO | 2017031225 A1 | 2/2017 |

*Primary Examiner* — Eduardo C Robert
*Assistant Examiner* — Michelle C Eckman

(57) ABSTRACT

A surgical instrument comprises an outer sleeve including an inner surface that defines a cavity. An inner shaft is fixed with the outer sleeve and extending within the cavity. The inner shaft includes a drive engageable with a first mating surface of a bone fastener. An inner sleeve is disposed between the inner shaft and the outer sleeve. The inner sleeve is rotatable relative to the outer sleeve and includes an element connectable with a second mating surface of the bone fastener. Systems, spinal implants and methods are disclosed.

19 Claims, 18 Drawing Sheets

(56) References Cited

U.S. PATENT DOCUMENTS

| | | | |
|---|---|---|---|
| 2008/0134434 A1 | 6/2008 | Celauro | |
| 2010/0037397 A1 | 2/2010 | Wood | |
| 2010/0249798 A1* | 9/2010 | Sournac | A61B 17/7076 606/104 |
| 2011/0046683 A1* | 2/2011 | Biedermann | A61B 17/7035 606/305 |
| 2012/0144689 A1 | 6/2012 | Skripps et al. | |
| 2013/0103039 A1* | 4/2013 | Hopkins | A61B 17/708 606/104 |
| 2013/0111666 A1 | 5/2013 | Jackson | |
| 2013/0261609 A1* | 10/2013 | Dicorleto | A61B 17/1622 606/1 |
| 2013/0282019 A1* | 10/2013 | Bouliane | A61B 17/7082 606/104 |
| 2013/0345718 A1* | 12/2013 | Crawford | A61B 17/025 606/130 |
| 2014/0100616 A1* | 4/2014 | Shipp | A61B 17/7082 606/86 A |
| 2014/0107708 A1* | 4/2014 | Biedermann | A61B 17/7082 606/278 |
| 2014/0109316 A1 | 4/2014 | Jackson et al. | |
| 2014/0371756 A1* | 12/2014 | Marigowda | A61B 17/7082 606/104 |
| 2015/0105831 A1* | 4/2015 | Yim | A61B 17/7091 606/86 A |
| 2015/0105833 A1* | 4/2015 | Simpson | A61B 5/06 606/86 R |
| 2015/0201985 A1* | 7/2015 | Rampersaud | A61B 17/8875 606/86 A |
| 2015/0201987 A1* | 7/2015 | Lemoine | A61B 17/8891 606/104 |
| 2015/0250512 A1* | 9/2015 | Poker | A61B 17/7037 606/305 |
| 2015/0257798 A1* | 9/2015 | Biedermann | A61B 17/7076 606/86 A |
| 2015/0282855 A1* | 10/2015 | Bess | A61B 17/8875 606/86 A |
| 2015/0359572 A1* | 12/2015 | Reimels | A61B 17/7082 606/104 |
| 2016/0030100 A1* | 2/2016 | Divincenzo | A61B 17/8875 606/104 |
| 2016/0047394 A1 | 2/2016 | Lee | |
| 2016/0262809 A1* | 9/2016 | May | A61B 17/1637 |
| 2016/0296266 A1* | 10/2016 | Chandanson | A61B 17/8875 |
| 2017/0049651 A1 | 2/2017 | Lim et al. | |
| 2017/0049653 A1 | 2/2017 | Lim et al. | |
| 2017/0079696 A1* | 3/2017 | Walker | A61B 17/708 |
| 2017/0333093 A1* | 11/2017 | Krier | A61B 17/7082 |
| 2018/0014863 A1* | 1/2018 | Biester | A61B 17/7076 |
| 2018/0042650 A1* | 2/2018 | Gao | A61B 17/7082 |
| 2018/0064497 A1* | 3/2018 | Hussain | A61B 34/32 |
| 2018/0147018 A1* | 5/2018 | Crawford | A61B 34/30 |
| 2018/0153591 A1* | 6/2018 | Schafer | A61B 17/8869 |
| 2018/0177536 A1* | 6/2018 | Divincenzo | A61B 17/7082 |
| 2018/0214190 A1* | 8/2018 | Erramilli | A61B 17/7082 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises an outer sleeve including an inner surface that defines a cavity. An inner shaft is fixed with the outer sleeve and extending within the cavity. The inner shaft includes a drive engageable with a first mating surface of a bone fastener. An inner sleeve is disposed between the inner shaft and the outer sleeve. The inner sleeve is rotatable relative to the outer sleeve and includes an element connectable with a second mating surface of the bone fastener. In some embodiments, systems, spinal implants and methods are disclosed.

In one embodiment, the surgical instrument includes an outer sleeve having an inner surface that defines an axial cavity. An inner shaft is fixed with the outer sleeve and extending within the cavity. The inner shaft includes a drive engageable with a drive socket of a bone fastener shaft. An inner sleeve is disposed between the inner shaft and the outer sleeve in a relative co-axial orientation. The inner sleeve is rotatable relative to the outer sleeve and includes an element connectable with an inner threaded surface of a bone fastener receiver. A rotatable actuator is connected with the inner sleeve and includes visual indicia of a non-locking configuration and a locking configuration with the inner threaded surface.

In one embodiment, a spinal implant system is provided. The spinal implant system comprises a surgical instrument including an outer sleeve and an inner shaft fixed with the outer sleeve and including a drive engageable with a bone fastener shaft, and an inner sleeve that is rotatable relative to the outer sleeve and including an element connectable with a threaded surface of a bone fastener receiver. A guide member includes an inner surface that defines a cavity configured for disposal of the outer sleeve and an image guide being oriented relative to a sensor to communicate a signal representative of a position of the guide member.

BRIEF DESCRIPTION OF THE DRAWINGS

The present disclosure will become more readily apparent from the specific description accompanied by the following drawings, in which.

DETAILED DESCRIPTION

Figure 1:
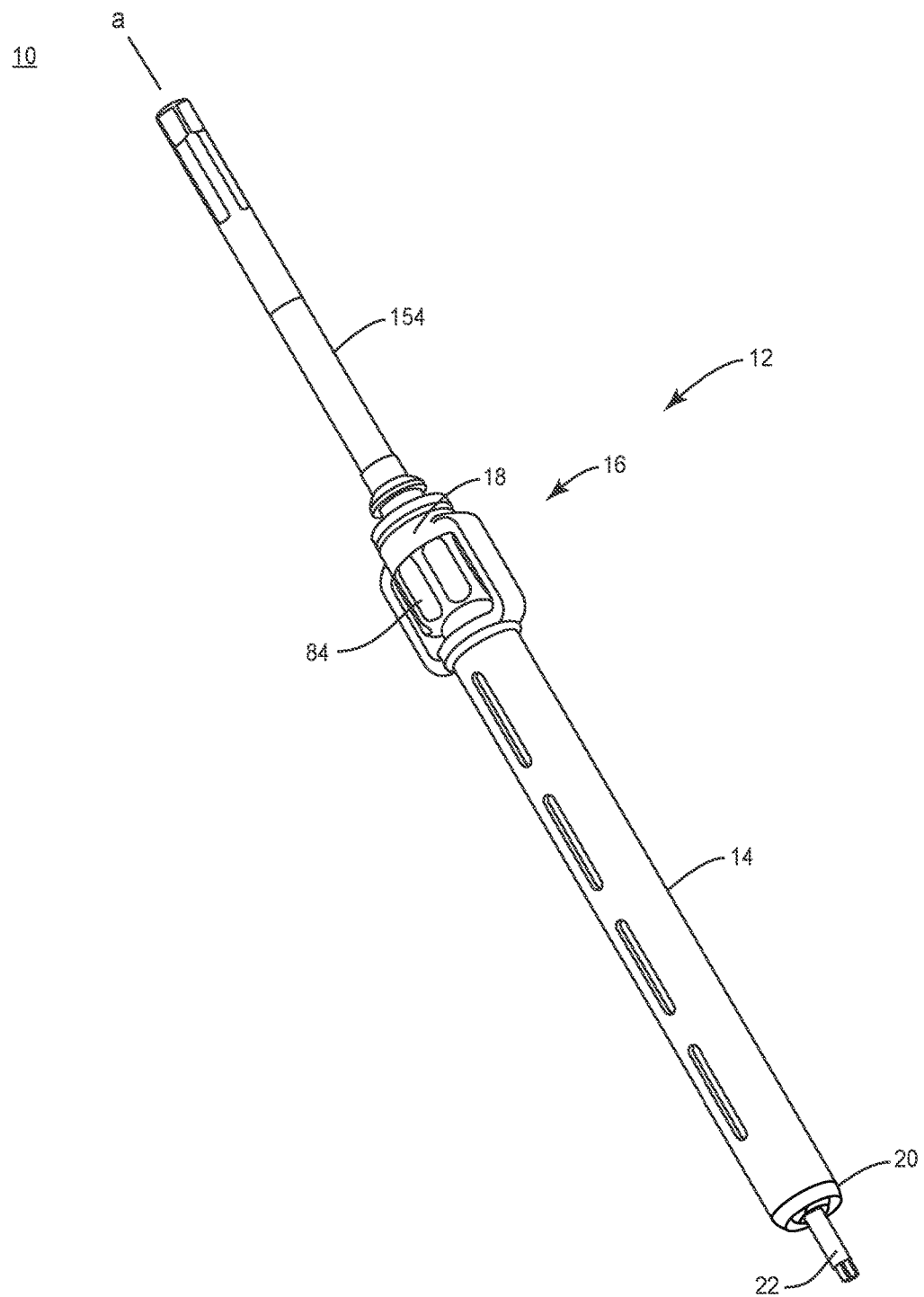
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a screw driver with a disengagement feature. In some embodiments, the driver is configured for use with a spinal implant, such as, for example, a bone fastener. The bone fastener may include open tulip head receivers and/or closed tulip head receivers. In some embodiments, the driver includes an outer sleeve and inner shaft that are configured as drive and guidance components. In some embodiments, the driver includes an inner sleeve configured with a screw to retain the bone fastener with the driver. In some embodiments, the inner shaft, inner sleeve and outer sleeve are co-axial to facilitate axial translation of the inner sleeve.

In some embodiments, the driver includes a knob that serves as a visual indicator of whether or not the driver is fully disengaged from an implant. In some embodiments, the screw driver is employed with robotic guidance and provides indicia of the driver being fully unthreaded from an implant. In some embodiments, the screw driver provides visual indicia that the screw driver is unthreaded from the implant in a minimally invasive surgical procedure. For example, the screw driver provides visual indicia whether the screw driver is or is not engaged.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a thumb wheel that is connected to a retention screw that threads into the bone screw.

In some embodiments, the driver includes an inner shaft having a Torx tip configured for engagement with the bone fastener. In some embodiments, upon engagement of the Torx tip with the bone fastener, an actuator, such as, for example, a thumb wheel is actuated to cause an inner sleeve and screw to tighten and pull the bone fastener into engagement with the driver. In some embodiments, the inner sleeve translates axially relative to the outer sleeve and the inner shaft. The outer sleeve is fixed to the inner shaft, such as, for example by welding.

In some embodiments, the present surgical system includes a screw driver that is employed with a method of use, which includes the step of retracting the inner sleeve. In some embodiments, the method of use includes the step of connecting the bone fastener with the Torx tip. In some embodiments, the method of use includes the step of actuating the knob to rotate the inner sleeve and the screw into engagement with the bone fastener.

In some embodiments, a co-axial orientation of the inner shaft, inner sleeve and outer sleeve allows the inner sleeve to relatively translate. In some embodiments, translation of the inner sleeve prevents disengagement of the bone fastener from the driver when being used with a robotic end effector. In some embodiments, this configuration facilitates use with bone fasteners having a closed tulip head configuration.

In some embodiments, the present surgical system includes a screw driver that is employed with a method of use, which includes the step of translating the inner sleeve into engagement with the bone fastener. In some embodiments, the method of use includes translating the inner sleeve in an opposite direction to disengage from the bone fastener. In some embodiments, the thumb wheel is configured to provide a visual indicator of whether the inner sleeve is engaged or disengaged with the bone fastener. In some embodiments, the visual indicator facilitates removal of the driver in minimally invasive surgical procedures.

In some embodiments, the present surgical system includes a screw driver that is employed with a method of assembling components of the present system, which includes the step of disposing a snap ring with a groove disposed with an inner surface of the thumb wheel. In some embodiments, the method includes the step of inserting the thumb wheel with the outer sleeve. In some embodiments, the method includes the step of inserting the inner shaft through the outer sleeve and thumb wheel, which retains the thumb wheel loosely. In some embodiments, the method includes the step of fixing and/or welding the inner shaft with the outer sleeve. In some embodiments, the method includes the step of inserting the inner sleeve into the outer sleeve and snap fitting the inner sleeve with the thumb wheel via the snap ring to retain the inner sleeve with the thumb wheel. In some embodiments, the inner sleeve and the thumb wheel include mating hexagonal features to form a keyed connection. In some embodiments, the inner shaft is fixed with and/or welded on to the outer sleeve to retain all internal components. In some embodiments, cleaning slots are providing for proper flushing/cleaning.

In some embodiments, the present surgical system includes a screw driver that is employed with a method of assembling components of the present system, which includes the step of initially inserting the thumb wheel with the outer sleeve. In some embodiments, the method includes the step of inserting the inner sleeve into the outer sleeve. In some embodiments, an opening disposed with the outer sleeve is sized to receive the inner sleeve to facilitate translation of the inner sleeve relative to the outer sleeve. In some embodiments, the method includes the step of engaging pins with the thumb wheel and the inner sleeve. In some embodiments, the method includes the step of laser welding the pins with the thumb wheel and the inner sleeve to relatively fix the thumb wheel and the inner sleeve. In some embodiments, the method includes the step of inserting the inner shaft through the outer sleeve and thumb wheel. In some embodiments, the method includes the step of fixing and/or welding the inner shaft with the outer sleeve.

In some embodiments, the present surgical system comprises a surgical instrument that comprises a screw driver that can be employed with bone fasteners and one or more implant supports for treating a spine. In some embodiments, the present surgical system includes a surgical instrument that can easily connect and disconnect from a bone fastener. In some embodiments, the present surgical system includes a surgical instrument that can be employed with an end effector of a robotic arm to facilitate implant with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system includes a screw driver having an outer shaft and a drive tip that engages a bone fastener. In some embodiments, the outer shaft and the drive tip are of one piece construction. In some embodiments, the one piece construction allows tolerances to be controlled tightly for improved accuracy of trajectory during implant insertion. In some embodiments, the drive tip includes a Torx configuration. In some embodiments, the present surgical system includes a screw driver having an internal retention mechanism. In some embodiments, the retention mechanism is fixed with a receiver of a bone fastener to resist and/or prevent disengagement of the retention mechanism from the receiver, for example, due to connection or friction with the end effector or tissue.

In some embodiments, the present surgical system includes a screw driver for use with robotic surgery. In some embodiments, the screw driver can be employed with fixed-axis screws (FAS), uni-axial screws (UAS), sagittal adjusting screws (SAS), transverse sagittal adjusting screws (TSAS) and multi-axial screws (MAS) screws, and allows the screws to be driven through a robotic end effector. In some embodiments, the screw driver includes a one piece outer sleeve having a tip. In some embodiments, the screw driver includes an internal retaining device that prevents accidental disengagement and/or unthreading.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a thumb wheel that is connected to a retention screw that threads into the bone screw. In some embodiments, the present surgical system includes tab extenders connected to the screw driver and prevented from extending outside the outside diameter of the screw driver by engaging undercuts of the screw driver. This configuration prevents an interference or hang-up if the bone screw needs to be removed through the end effector.

In some embodiments, the present surgical system includes a screw driver that includes a quick connect shaft, an inner shaft, a thumb wheel, an outer driver shaft and a retention screw. In some embodiments, the retention screw is axially translatable between a first position, for example, a non-locking position prior to tightening, and a second position, for example, a locking position after tightening. In some embodiments, this configuration allows the drive tip to engage the bone screw prior to rotating the thumb wheel for tightening the screw driver to the bone screw.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-16, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a driver 12. Driver 12 can be employed with an end effector 200 (FIG. 10) of a robotic arm R (FIG. 16) to facilitate implant with robotic arm R. Driver 12 is guided through end effector 200 for guide-wireless insertion of a spinal implant, such as, for example, a bone fastener 100, as described herein.

Driver 12 includes a member, such as, for example, an outer tubular sleeve 14. Outer sleeve 14 extends between a proximal end 18 and a distal end 20. Outer sleeve 14 defines a longitudinal axis a. In some embodiments, outer sleeve 14 may have various configurations including, for example, round, oval, polygonal, irregular, consistent, variable, uniform and non-uniform. Outer sleeve 14 includes a diameter D1. In some embodiments, diameter D1 is slightly larger than a screw spin diameter D2 of bone fastener 100. This configuration allows bone fastener 100 and driver 12 to pass through end effector 200 of the robotic arm, as described herein.

Figure 9:
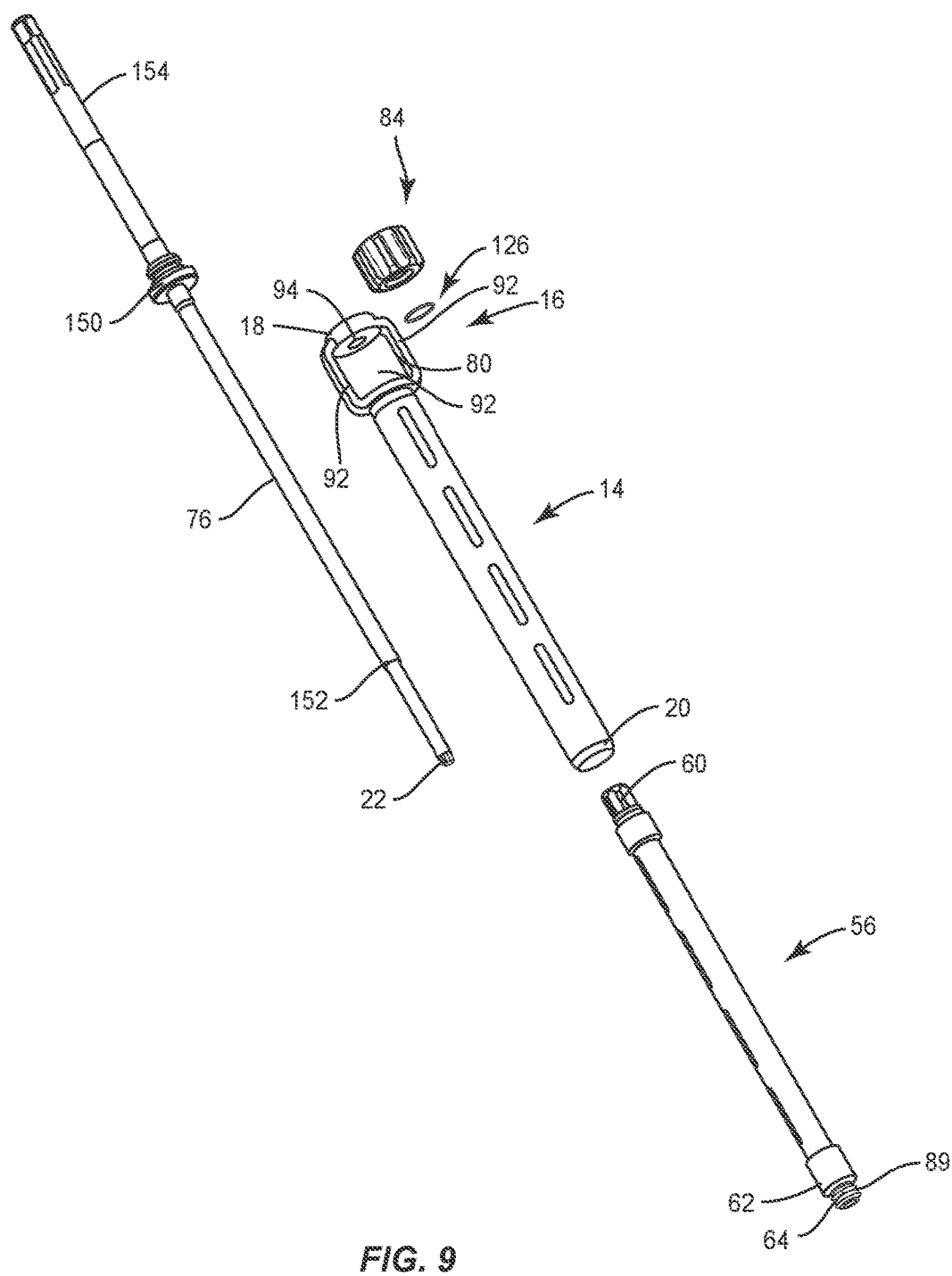
FIG. 9 is a perspective view of components of one embodiment of a surgical system in accordance with the principles of the present disclosure with parts separated.
Figure 10:
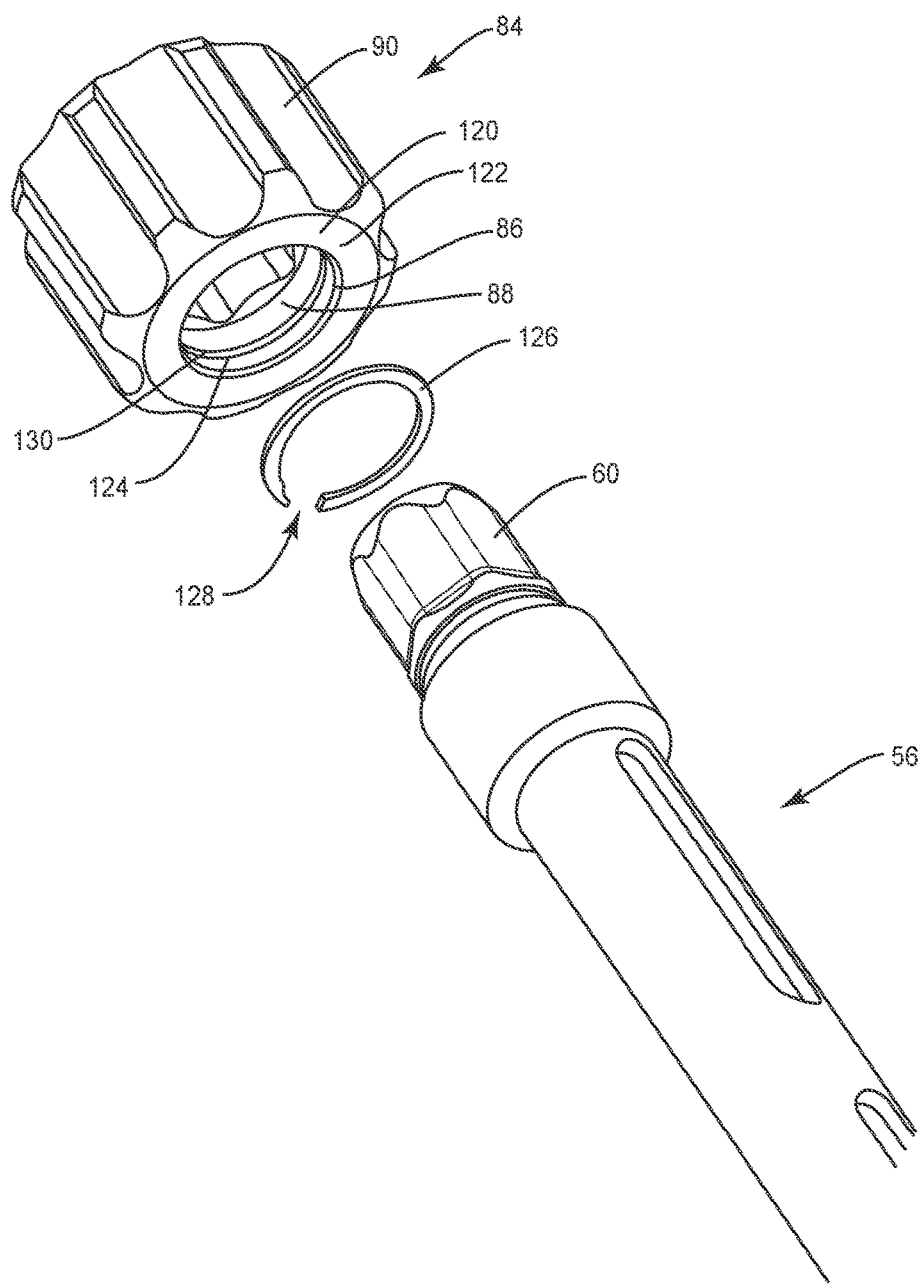
FIG. 10 is a break away perspective view of components of one embodiment of a surgical system in accordance with the principles of the present disclosure.
Figure 11:
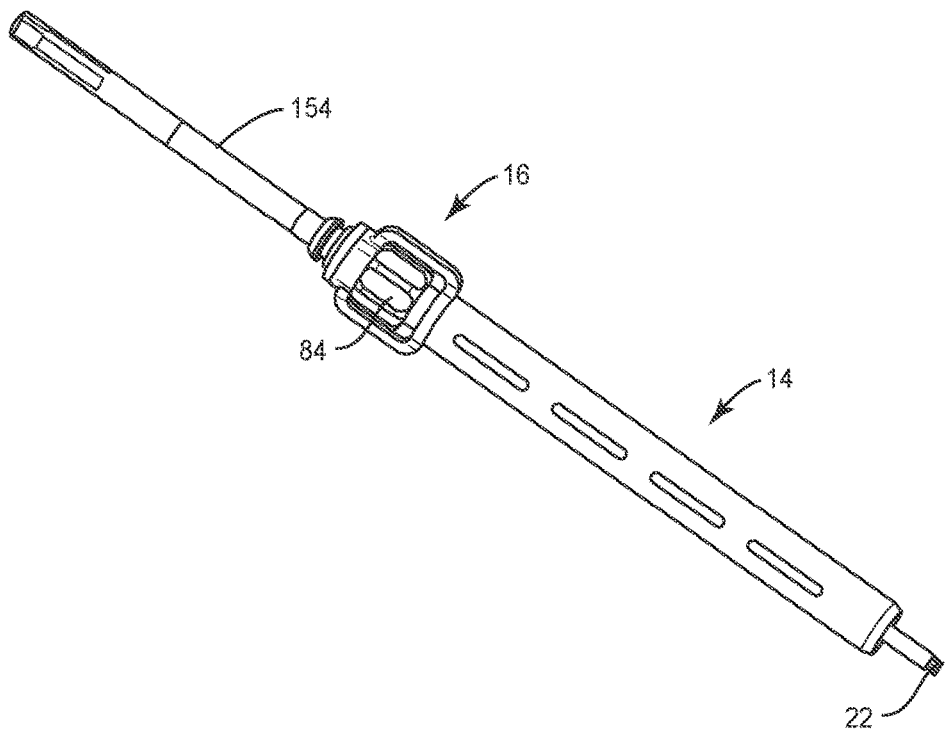
FIG. 11 is a perspective view of components of one embodiment of a surgical system in accordance with the principles of the present disclosure.
Figure 12:
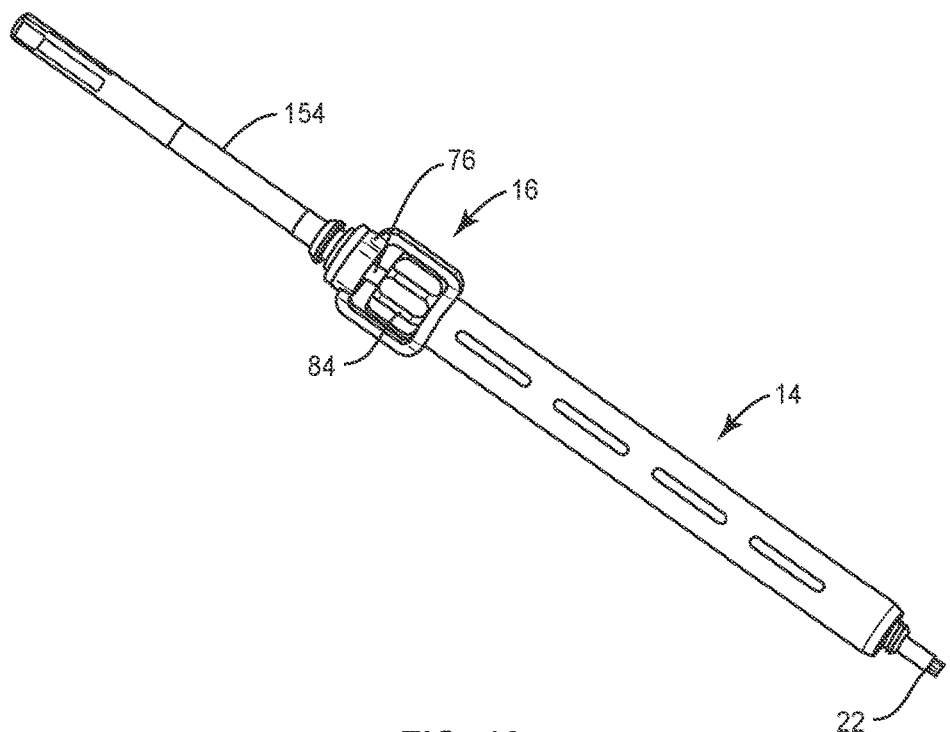
FIG. 12 is a perspective view of the components shown in FIG. 12.
Figure 13:
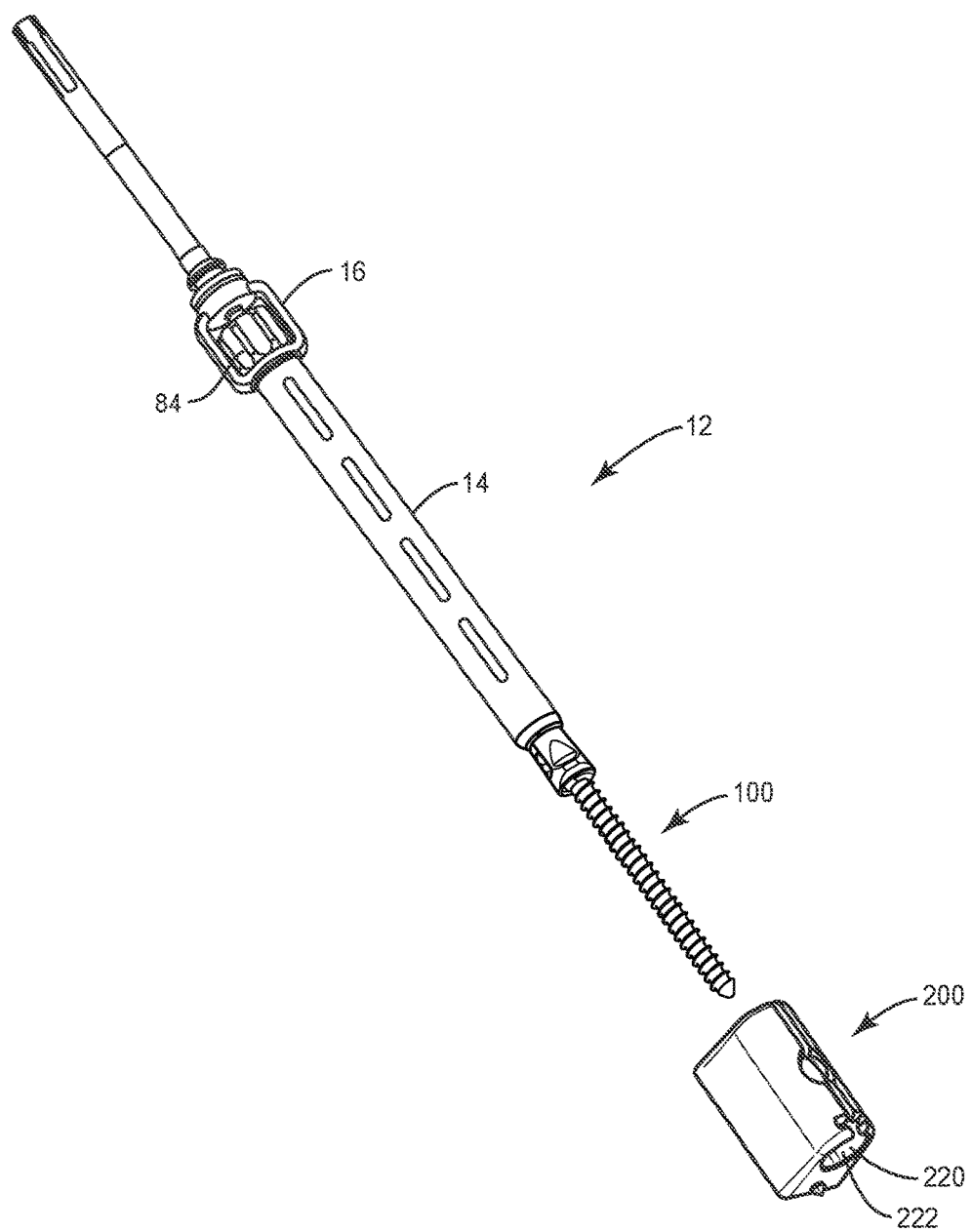
FIG. 13 is a perspective view of components of one embodiment of a surgical system in accordance with the principles of the present disclosure.
Figure 14:
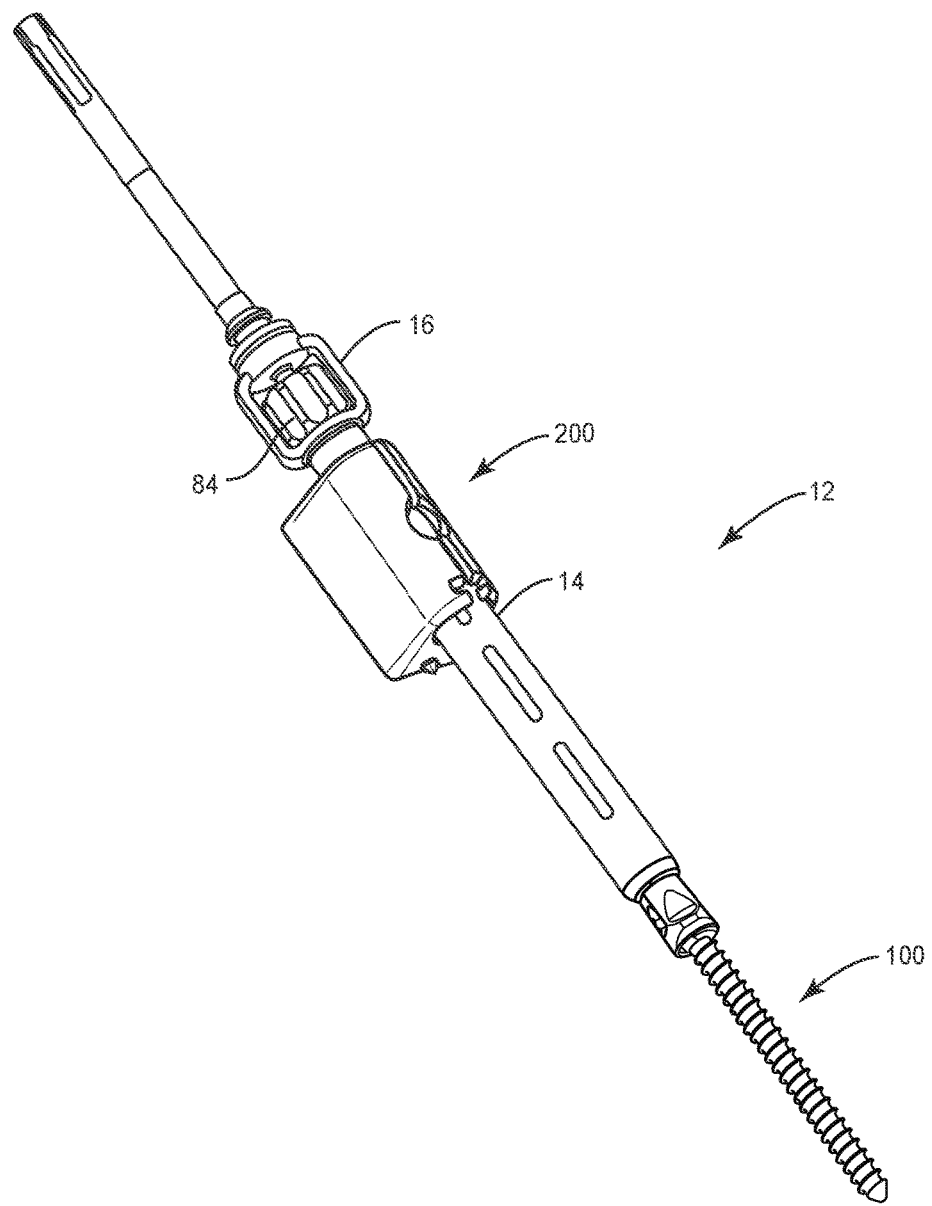
FIG. 14 is a perspective view of the components shown in FIG. 13.

Outer sleeve 14 includes a surface 50 that defines an axial cavity 52. Cavity 52 is configured for disposal of an inner sleeve 56 and an inner shaft 76, as described herein. Outer sleeve 14 includes a collar body 16 having a surface 80. Surface 80 defines a cavity 82. Body 16 includes bifurcated arms 92 disposed about cavity 82 to facilitate disposal and access to an actuator, such as, for example, a thumb wheel 84 therein. Body 16 includes opening 94 disposed at end 18. Opening 94 is in communication with cavity 82 and in alignment with cavity 52 to facilitate insertion of inner shaft 76 into end 18, through wheel 84 and into cavity 52 for assembly, as described herein. Wheel 84 is configured to actuate rotation of inner sleeve 56 and an engagement element, such as, for example, a screw 64, as described herein. Wheel 84 includes a surface 86 that defines a cavity 88. Cavity 88 is configured for disposal of a correspondingly shaped portion of inner sleeve 56, as shown in FIGS. 9 and 10.

Wheel 84 includes a wall 120 having a surface 122. Surface 122 defines a groove 124 configured for disposal of a band, such as, for example, a circumferential ring 126, as shown in FIG. 10. Ring 126 includes a circumference that extends between ends defining an opening, such as, for example, a gap 128, which facilitates expansion and contraction of ring 126. Groove 124 includes a portion, such as, for example, a circumferential channel 130. In some embodiments, inner sleeve 56 is manually engageable with wheel 84 in a snap-fit assembly such that ring 126 translates into channel 130 to capture inner sleeve 56. Ring 126 is expandable and resilient between a contracted and/or capture orientation and an expanded orientation, as described herein.

Inner sleeve 56 extends between an end 60 and an end 62. End 60 is engageable with wheel 84. Wheel 84 actuates rotation of inner sleeve 56 and screw 64, as described herein. Surface 86 engages end 60 in an interference fit to facilitate simultaneous rotation of wheel 84, inner sleeve 56 and screw 64. In some embodiments, surface 86 defines a hexagonal cross section of cavity 88 for a mating engagement with correspondingly shaped end 60 of inner sleeve 56. In some embodiments, cavity 88 includes various configurations, such as, for example, hexalobe, cruciform, phillips, square, polygonal, star cross sectional configuration for a mating engagement with correspondingly shaped portion of inner sleeve 56. In some embodiments, wheel 84 includes a surface 90 configured to facilitate gripping of wheel 84, such as, for example a knurled surface.

Assembly of inner sleeve 56 with wheel 84 includes aligning end 60 with cavity 88. End 60 translates through and relative to ring 126 to move ring 126 into an expanded orientation, as described herein. Ring 126 is resiliently biased to the capture orientation such that inner sleeve 56 is attached with wheel 84, as described herein. Disengagement of inner sleeve 56 from wheel 84 is resisted and/or prevented. Ring 126 is configured to resist and/or prevent axial translation of inner sleeve 56 relative to wheel 84

Inner sleeve 56 includes an inner surface 66. Surface 66 defines an axial channel 68 configured for moveable disposal of inner shaft 76, as described herein. Channel 68 extends co-axial with cavity 52. In some embodiments, channel 68 is disposed at alternate orientations relative to axis a, such as, for example, at transverse, perpendicular and/or other angular orientations such as acute or obtuse, and/or may be offset or staggered. End 62 of inner sleeve 56 includes screw 64. Screw 64 includes an outer surface having a thread form 89. Thread form 89 is configured for engagement with a mating surface, such as, for example, thread forms of arms 104, 106 of bone fastener 100 to pull and or draw bone fastener 100 into engagement with driver 12, as described herein.

Figure 3:
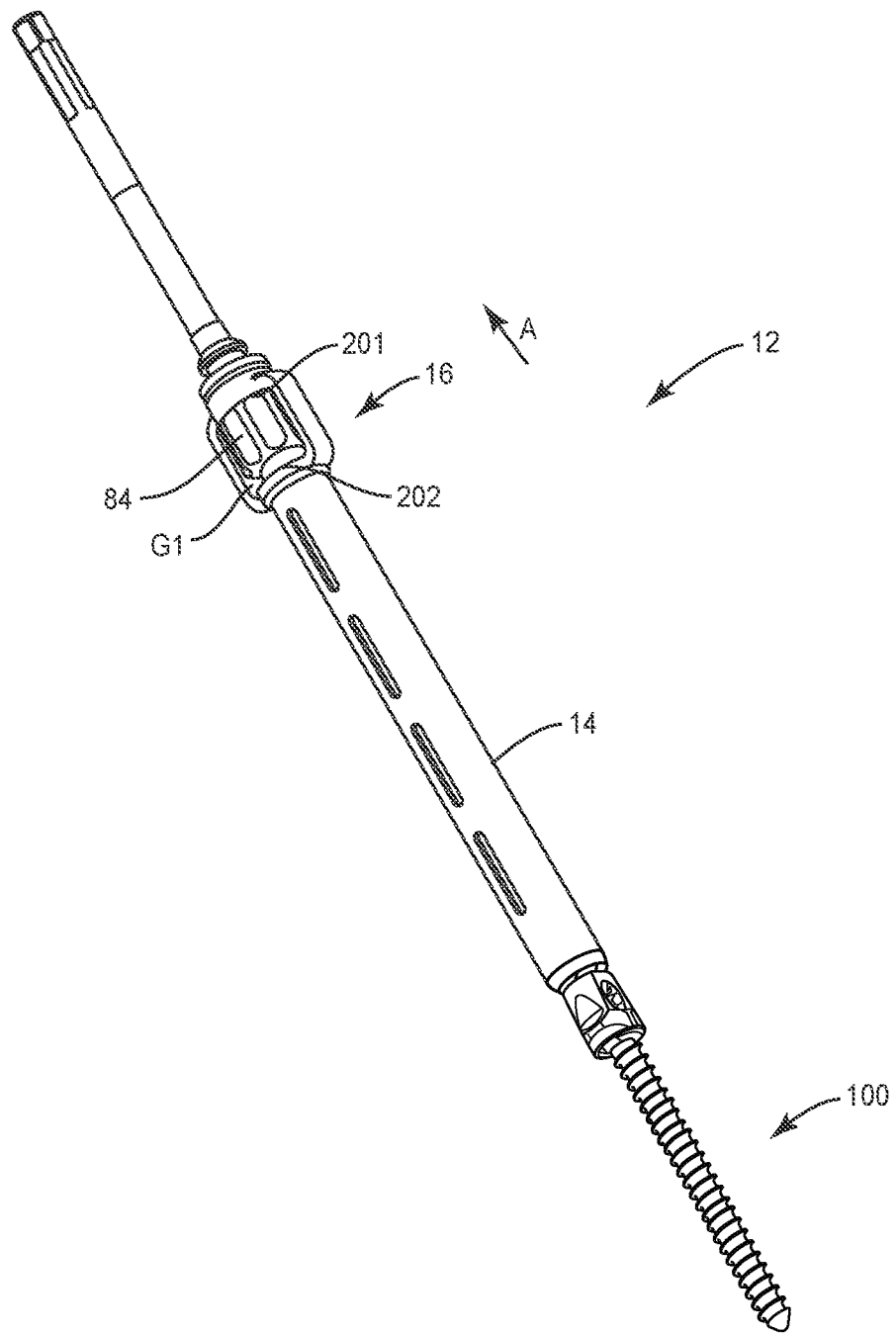
FIG. 3 is a perspective view of the components of the surgical system shown in FIG. 2.
Figure 4:
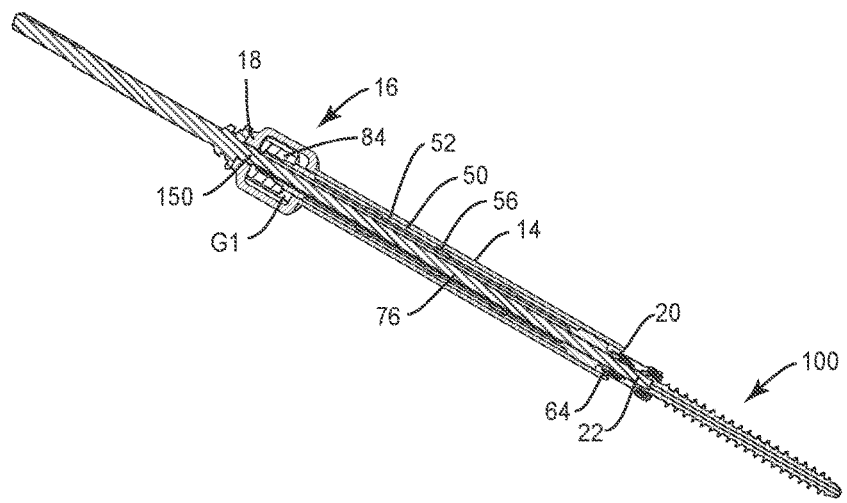
FIG. 4 is a cross section view of the components shown in FIG. 3.
Figure 5:
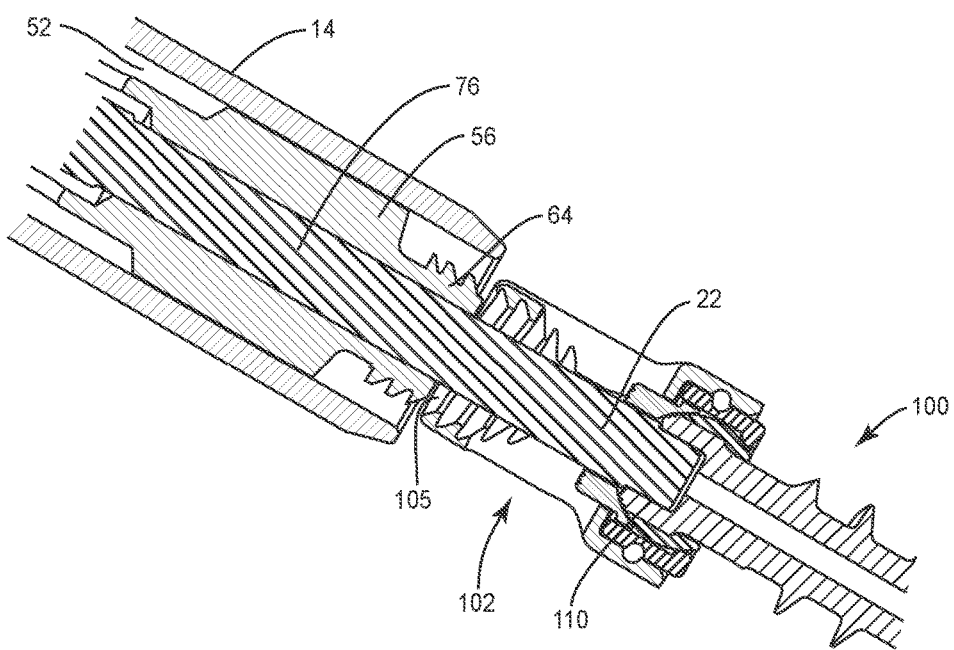
FIG. 5 is a break away view of the components shown in FIG. 4.
Figure 6:
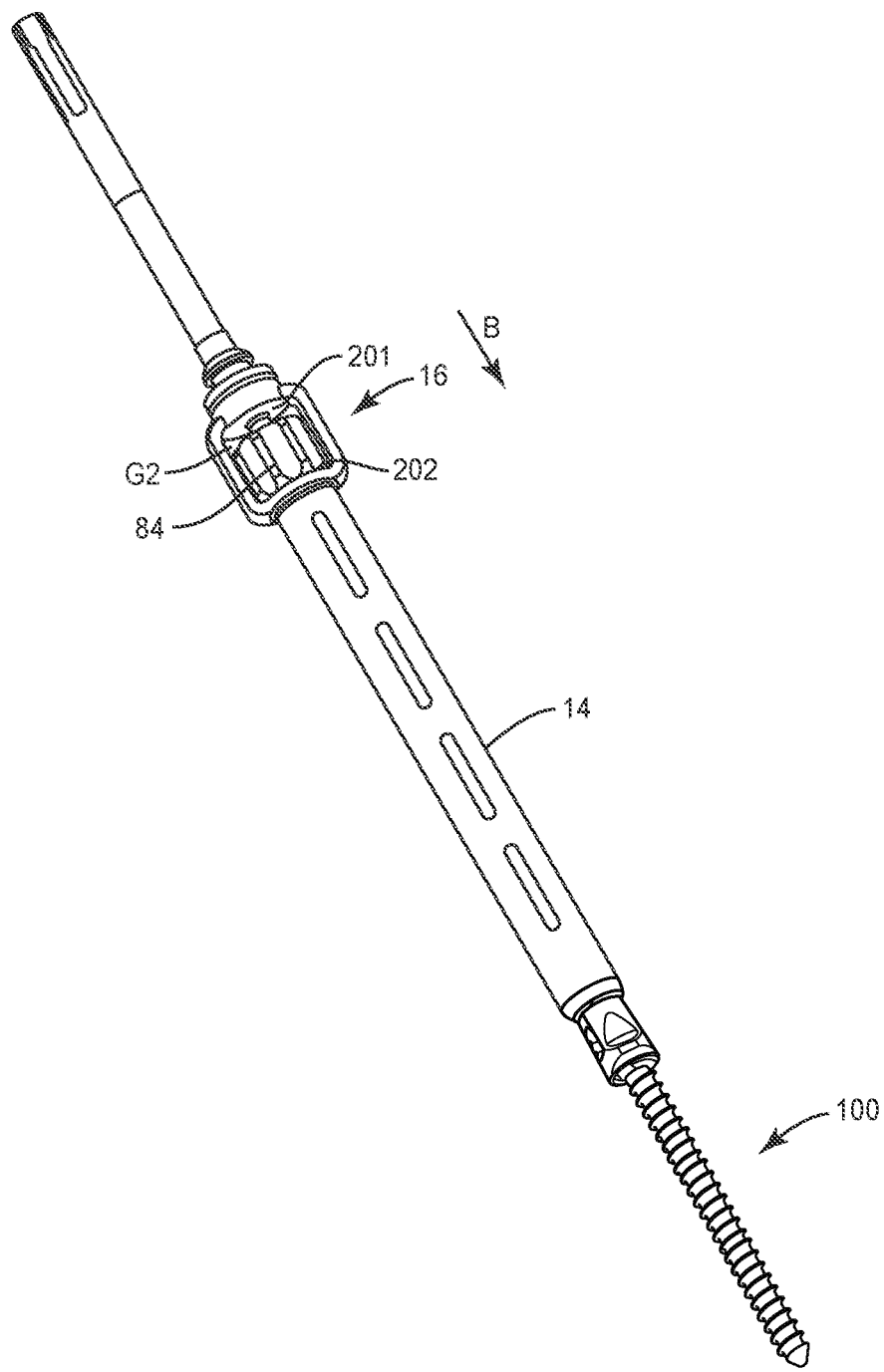
FIG. 6 is a perspective view of the components of the surgical system shown in FIG. 2.
Figure 7:
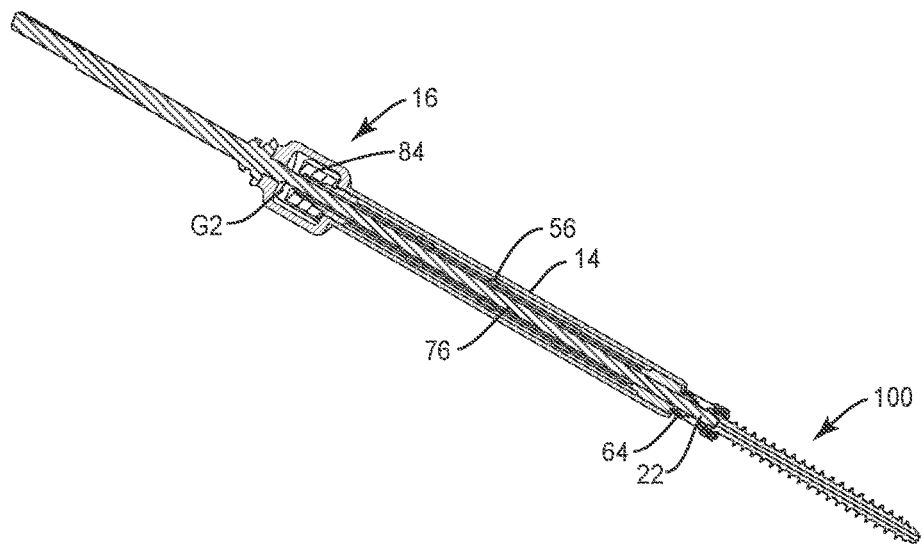
FIG. 7 is a cross section view of the components shown in FIG. 6.
Figure 8:
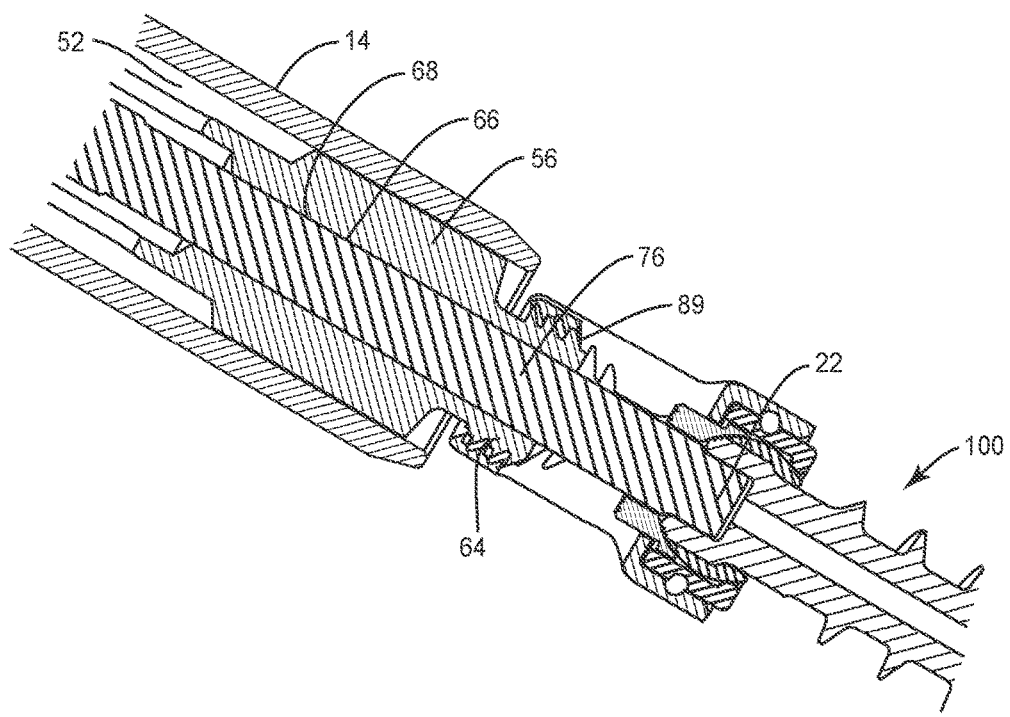
FIG. 8 is a break away view of the components shown in FIG. 7.

Wheel 84 is translatable within cavity 82 causing simultaneous axial movement of inner sleeve 56 and screw 64 relative to outer sleeve 14. Body 16 includes ends 201, 202 that define a range of axial translation of wheel 84 relative to outer sleeve 14. Wheel 84 is moveable relative to outer sleeve 14 between a proximal position and a distal position. In the proximal position, wheel 84 provides visual indicia of a non-locking configuration of screw 64 relative to bone fastener 100, as shown in FIGS. 3-5. In the distal position, wheel 84 provides visual indicia of a locking configuration of screw 64 relative to bone fastener 100, as shown in FIGS. 6-8.

Wheel 84 provides visual indicia displaying the locking and/or non-locking configuration of screw 64 by a position of wheel 84 relative to outer sleeve 14. For example, wheel 84 is disposed or translates, in a direction shown by arrow A in FIG. 3, such that a gap G1 is viewable. Gap G1 is disposed between wheel 84 and end 202. Gap G1 is viewable to indicate that screw 64 is disposed in the non-locking configuration relative to bone fastener 100. Wheel 84 is translatable, in a direction shown by arrow B in FIG. 6, closing gap G1 such that a gap G2 is viewable. Gap G2 is disposed between wheel 84 and end 201. Gap G2 is viewable to indicate that screw 64 is disposed in the locking configuration relative to bone fastener 100. In some embodiments, translation of wheel 84 and the visual indicia indicating the disengaged, non-locking configuration of screw 64 relative to bone fastener 100 facilitates removal of driver 12 in minimally invasive surgical procedures.

In some embodiments, the indicia of a non-locking and/or a locking configuration may include alternative visual indicia, tactile indicia, audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, the indicia includes a notch, slot, bead, detent, bump, print, label, score, color coding and/or cavity disposed on wheel 84. In some embodiments, the indicia may be attachable with or adhered to wheel 84.

Figure 15:
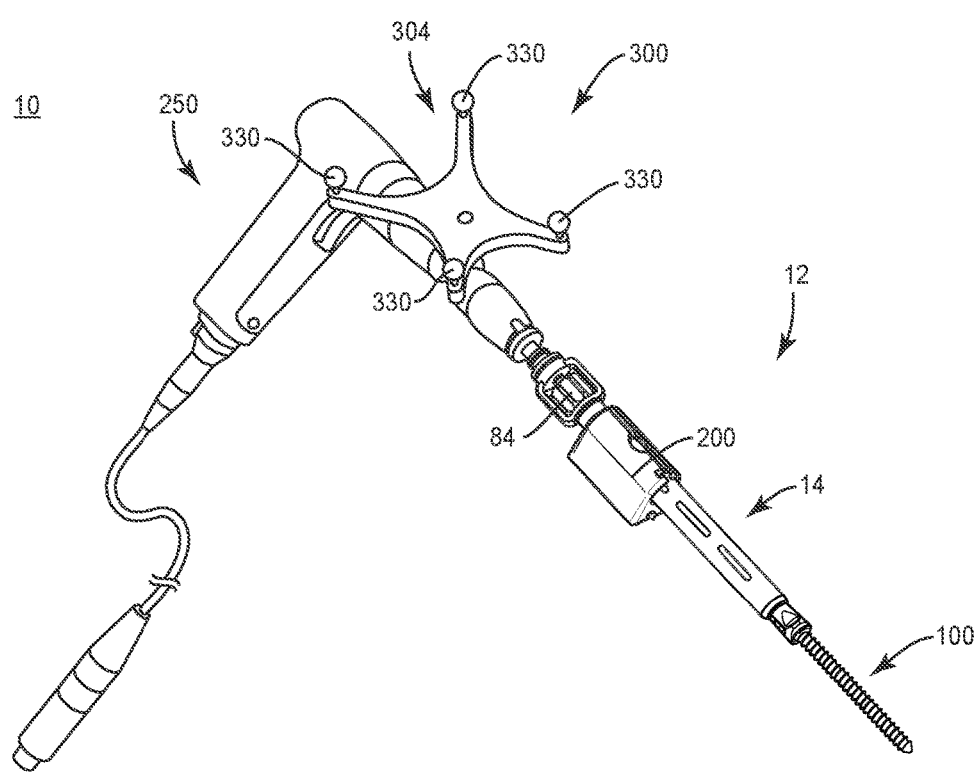
FIG. 15 is a perspective view of components one embodiment of a surgical system in accordance with the principles of the present disclosure.

Inner shaft 76 extends between an end 150 and an end 152. Inner shaft 76 is disposable with channel 68, as described herein. End 150 is fixed with outer sleeve 14 such that rotation of inner shaft 76 causes simultaneous rotation of outer sleeve 14. In some embodiments, inner shaft 76 is welded with outer sleeve 14. Inner shaft 76 is rotatable independently of inner sleeve 56 such that rotation of inner shaft 76 to engage bone fastener 100 is separate and apart from rotation of inner sleeve 56 and screw 64. In some embodiments, inner shaft 76 includes a portion 154 configured to facilitate connection of driver 12 with a surgical instrument, such as, for example, an actuator/drill 250, as shown in FIG. 15. In some embodiments, inner shaft 76 includes quick connect surfaces or keyed geometry, such as, for example, triangle, hex, square or hexalobe to facilitate connection with actuator 250.

End 152 of inner shaft 76 includes a distal tip, such as, for example, drive 22, as shown in FIG. 1. Drive 22 is integrally connected or monolithically formed with inner shaft 76. This configuration facilitates control of tolerances to optimize accuracy of the connection of inner shaft 76 with bone fastener 100. Drive 22 is engageable with a spinal implant, such as, for example, bone fastener 100. For example, drive 22 fits with and is engageable with a mating surface, such as, for example, a socket 110 of bone fastener 100. Rotation of inner shaft 76 simultaneously rotates drive 22 to drive, torque, insert or otherwise connect bone fastener 100 with tissue, as described herein. In some embodiments, drive 22 includes a hexalobe geometry for a mating engagement with a correspondingly shaped socket 110. In some embodiments, drive 22 can alternatively include a cruciform, phillips, square, hexagonal, polygonal, star cross sectional configuration for disposal of a correspondingly shaped socket 110.

Wheel 84 is inserted laterally into cavity 82. Inner shaft 76 is inserted from end 18, through opening 94, through cavity 88 to provisionally connect wheel 84 with outer sleeve 14. Inner shaft 76 is welded to outer sleeve 14. Inner sleeve 56 is inserted from end 20 of outer sleeve 14 into engagement with wheel 84, as described herein. Inner shaft 76 is disposed with cavity 68 of inner sleeve 56. Inner sleeve 56 is rotatable relative to outer sleeve 14 and inner shaft 76. Inner shaft 76 and outer sleeve 14 simultaneously rotate relative to inner sleeve 56.

Figure 2:
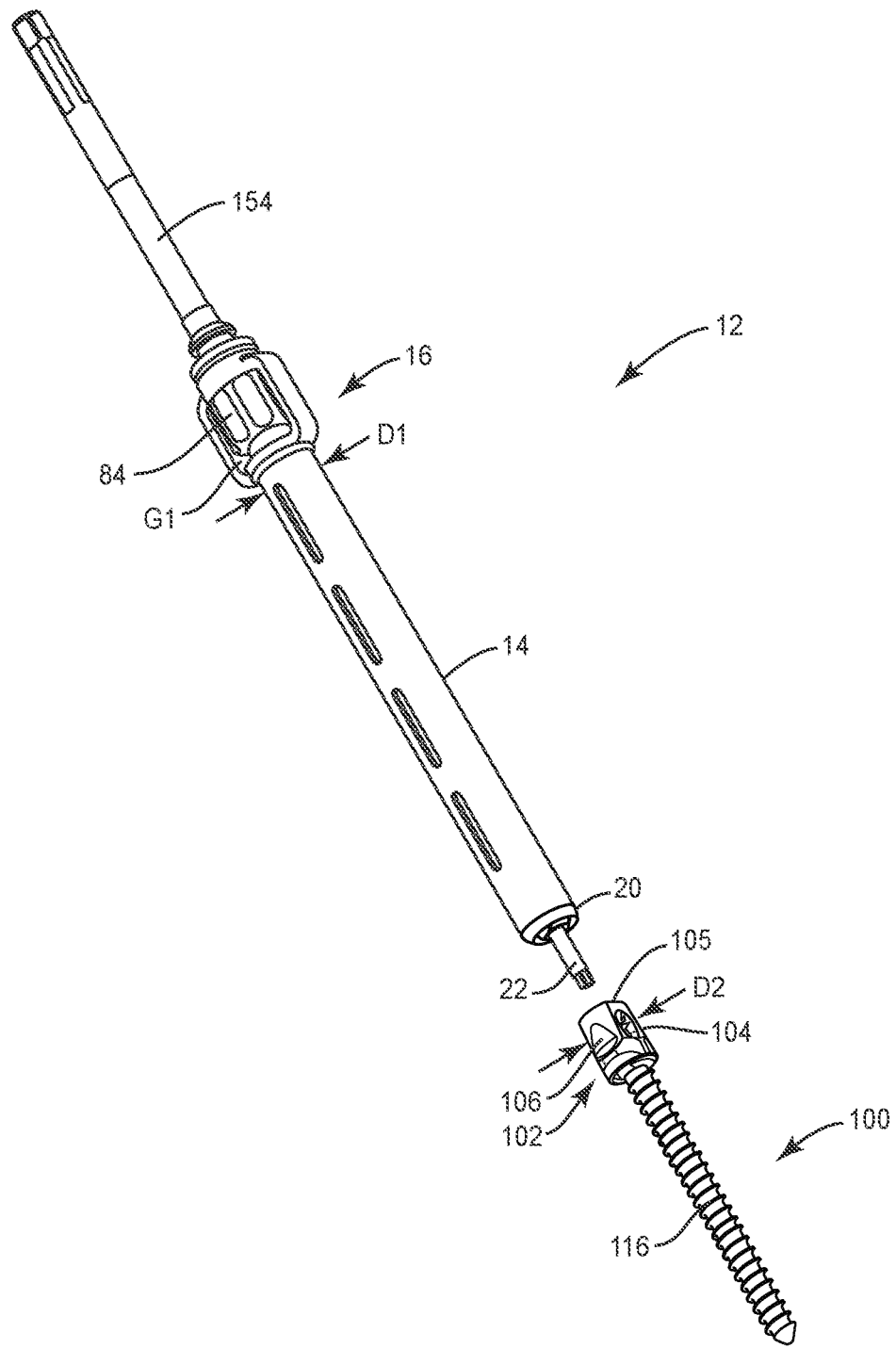
FIG. 2 is a perspective view of components of one embodiment of a surgical system in accordance with the principles of the present disclosure.

Bone fastener 100 includes receiver 102. Receiver 102 extends along axis a when connected with outer sleeve 14. Receiver 102 includes a pair of spaced apart arms 104, 106 that define an implant cavity configured for disposal of a component of a spinal construct, such as, for example, a spinal rod (not shown). Arms 104, 106 are connected at proximal ends of receiver 102 to define a closed tulip bone screw including a closed spinal rod slot, as shown in FIG. 2. Receiver 102 defines an opening 105 between arms 104, 106. In some embodiments, receiver 102 comprises an open tulip bone screw head.

Receiver 102 includes socket 110 configured for engagement with drive 22, as described herein. Receiver 102 includes an inner surface having a thread form located adjacent arm 104 and a thread form located adjacent arm 106. The thread forms of arms 104, 106 are configured for engagement with thread form 89 to retain bone fastener 100 with driver 12, as described herein. Bone fastener 100 includes a threaded shaft 116. Shaft 116 is configured to penetrate tissue, such as, for example, bone.

In use, drive 22 is aligned with closed receiver 102 and passed through opening 105 for disposal with socket 110, as shown in FIG. 2. Bone fastener 100 is connected with driver 12. Drive 22 is engaged with socket 110 and screw 64 is disposed with inner sleeve 56 and assembled with outer sleeve 14 for axial translation relative to outer sleeve 14 and along inner shaft 76 between a non-locking configuration, as shown in FIGS. 3-5, and a locking configuration, as shown in FIGS. 6-8, with a spinal implant, such as, for example, bone fastener 100.

Wheel 84 is disposed in the proximal position and provides visual indicia, including gap G1, of the non-locking configuration of screw 64 relative to bone fastener 100, as shown in FIG. 4. Drive 22 is engaged with socket 110 such that bone fastener 100 is connected with outer sleeve 14, and thread form 89 is aligned with the thread forms of arms 104, 106 for engagement therebetween to retain bone fastener 100 with driver 12, as shown in FIG. 5. Wheel 84 is manipulated for rotation such that inner sleeve 56 rotates screw 64 relative to and independent of outer sleeve 14. Screw 64 is aligned with closed receiver 102 and passed through opening 105. Thread form 89 engages the thread forms of arms 104, 106 and inner sleeve 56 axially translates screw 64 into receiver 102. The threaded engagement of screw 64 and receiver 102 pulls and/or draws bone fastener 100 into the locking configuration with driver 12 for releasable fixation therebetween, as shown in FIG. 8. Wheel 84 is disposed in the distal position and provides visual indicia, including gap G2, of the locking configuration of screw 64 relative to bone fastener 100, as shown in FIGS. 6 and 7.

Inner shaft 76 with drive 22 is connected with outer sleeve 14, as described herein, and inner shaft 76 and outer sleeve 14 are rotated to drive, torque, insert or otherwise connect bone fastener 100 with adjacent tissue. Screw 64 remains releasably fixed with receiver 102, independent of inner shaft 76 and outer sleeve 14 rotation and/or engagement or friction with components of spinal implant system 10 as described herein, to resist and/or prevent disengagement or unthreading of screw 64 from receiver 102. In some embodiments, wheel 84 is manipulated for rotation such that inner sleeve 56 and screw 64 rotates relative to outer sleeve 14, and thread form 89 disengages the thread forms of arms 104, 106. Screw 64 axially translates from receiver 102 to unthread driver 12 from receiver 102 such that wheel 84 is disposed in the proximal position and provides visual indicia, including gap G1, of the non-locking configuration of screw 64 relative to bone fastener 100, as shown in FIGS. 3 and 4.

Figure 16:
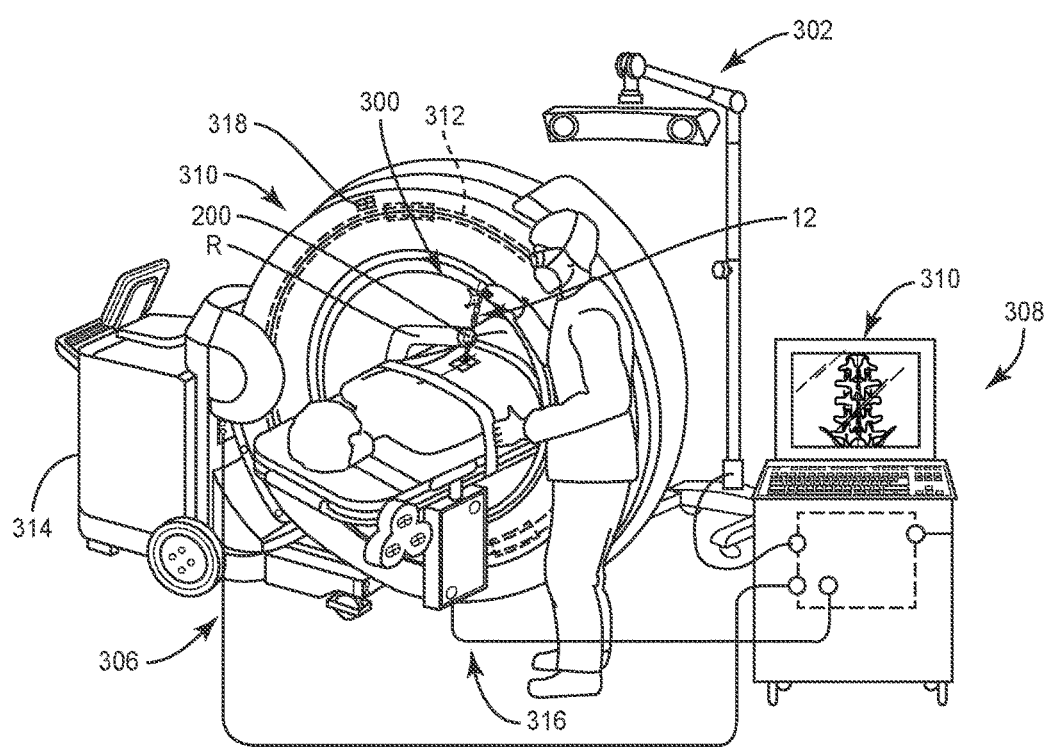
FIG. 16 is a perspective view of components of one embodiment of a surgical system in accordance with the principles of the present disclosure.
Figure 17:
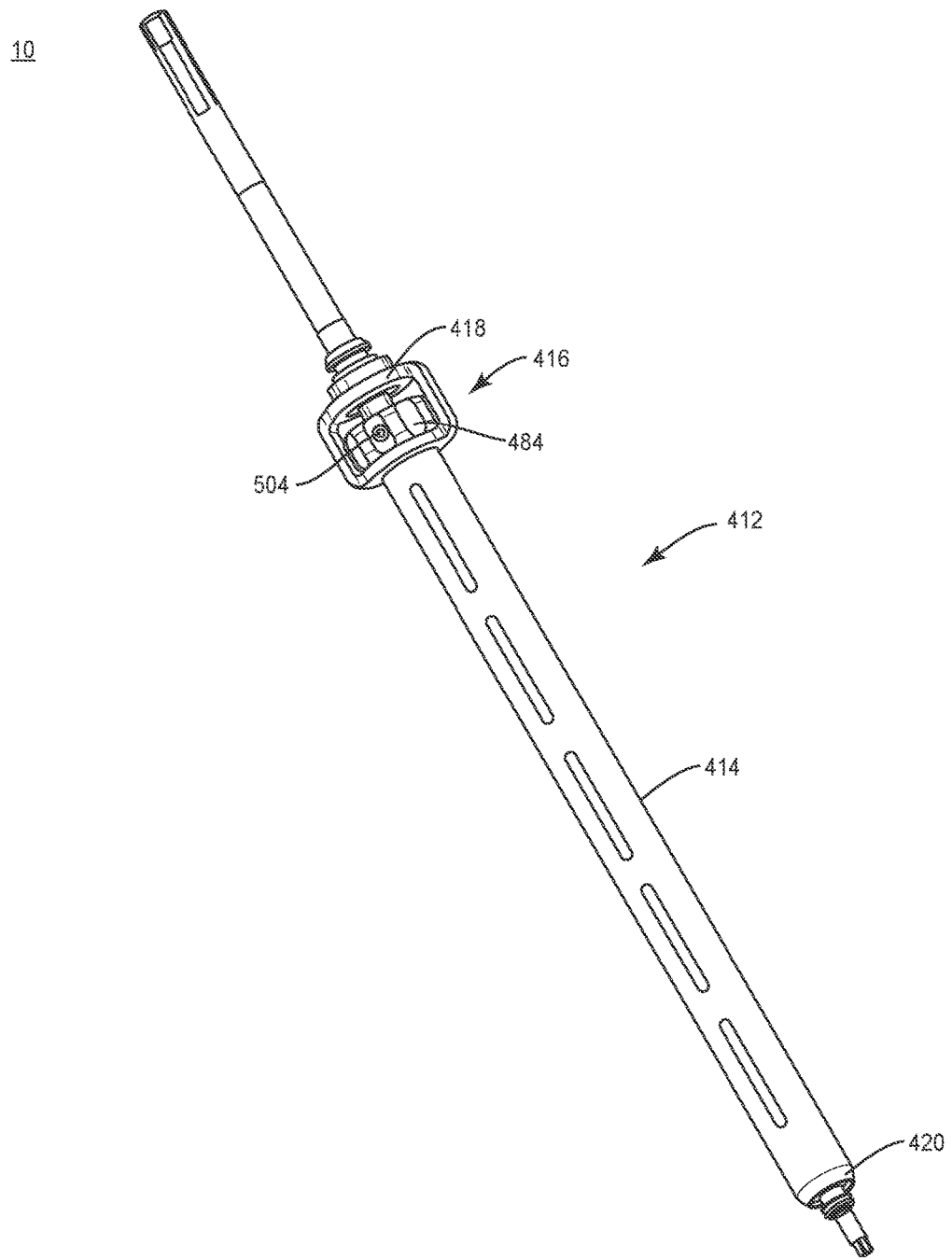
FIG. 17 is a perspective view of components one embodiment of a surgical system in accordance with the principles of the present disclosure.

In some embodiments, driver 12 includes a navigation component 300, as shown in FIGS. 15 and 16. Driver 12 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of bone fastener 100 relative to driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 300 is connected with portion 154 or outer sleeve 14 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of a surgical navigation system 306, as shown in FIG. 16 and described herein. In some embodiments, the signal generated by emitter array 304 represents a position of bone fastener 100 relative to driver 12 and relative to tissue, such as, for example, bone. In some embodiments, the signal generated by emitter array 304 represents a three dimensional position of bone fastener 100 relative to tissue.

In some embodiments, sensor array 302 receives signals from emitter array 304 to provide a three-dimensional spatial position and/or a trajectory of bone fastener 100 relative to driver 12 and/or tissue. Emitter array 304 communicates with a processor of computer 308 of navigation system 306 to generate data for display of an image on monitor 310, as described herein. In some embodiments, sensor array 302 receives signals from emitter array 304 to provide a visual representation of a position of bone fastener 100 relative to driver 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, such as, for example, x-ray images appropriate for a given surgical procedure. In some embodiments, pre-acquired images of a patient are collected. In some embodiments, surgical navigation system 306 can include an O-arm® imaging device 310 sold by Medtronic Navigation, Inc. having a place of business in Louisville, Colo., USA. Imaging device 310 may have a generally annular gantry housing that encloses an image capturing portion 312.

In some embodiments, navigation system 306 comprises an image capturing portion 314 that may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 318, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 314 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to driver 12 and/or tissue can be tracked. Sensor array 302 is located in such a manner to provide a clear line of sight with emitter array 304, as described herein. In some embodiments, fiducial markers 330 of emitter array 304 communicate with sensor array 302 via infrared technology. Sensor array 302 is coupled to computer 308, which may be programmed with software modules that analyze signals transmitted by sensor array 302 to determine the position of each object in a detector space.

Driver 12 is configured for use with a guide member, such as, for example, an end effector 200 of a robotic arm R. End effector 200 includes a surface 220 that defines a cavity, such as, for example, a channel 222. Channel 222 is configured for passage of bone fastener 100 and disposal of driver 12. Robotic arm R includes position sensors (not shown), similar to those referenced herein, which measure, sample, capture and/or identify positional data points of end effector 200 in three dimensional space for a guide-wireless insertion of bone fasteners 100 with selected vertebral levels. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three dimensional space, which are communicated to computer 308.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving bone fasteners 100. Drive 22 is aligned with closed receiver 102 and passed through opening 105 for disposal with socket 110, as shown in FIG. 2. Bone fastener 100 is connected with driver 12. Drive 22 is engaged with socket 110 and screw 64 is disposed with inner sleeve 56 for axial translation relative to outer sleeve 14 between a non-locking configuration, as shown in FIGS. 3-5, and a locking configuration, as shown in FIGS. 6-8, with bone fastener 100.

Wheel 84 is disposed in the proximal position and provides visual indicia, including gap G1, of the non-locking configuration of screw 64 relative to bone fastener 100, as shown in FIG. 4. Thread form 89 is aligned with the thread forms of arms 104, 106 for engagement therebetween to retain bone fastener 100 with driver 12, as shown in FIG. 5. Wheel 84 is manipulated for rotation such that inner sleeve 56 rotates screw 64 relative to and independent of outer sleeve 14. Screw 64 is aligned with closed receiver 102 and passed through opening 105. Thread form 89 engages the thread forms of arms 104, 106 and inner sleeve 56 axially translates screw 64 into receiver 102. The threaded engagement of screw 64 and receiver 102 pulls and/or draws bone fastener 100 into the locking configuration with driver 12 for releasable fixation therebetween, as shown in FIG. 8. Wheel 84 is disposed in the distal position and provides visual indicia, including gap G2, of the locking configuration of screw 64 relative to bone fastener 100, as shown in FIGS. 6 and 7.

Driver 12, connected with bone fastener 100, is oriented for disposal with end effector 200 of robotic arm R, as described herein. The assembly of driver 12/bone fastener 100 is disposed with channel 220 for implantation of one or more bone fasteners 100 with vertebrae employing robotic arm R and/or surgical navigation system 306, as described herein. Actuator 250 is connected with inner shaft 76 and drive 22 engages bone fastener 100, as described herein, and inner shaft 76 and outer sleeve 14 are rotated to drive, torque, insert or otherwise connect bone fastener 100 with adjacent tissue. Screw 64 remains releasably fixed with receiver 102, independent of inner shaft 76 and outer sleeve 14 rotation and/or engagement or friction with end effector 200 to resist and/or prevent disengagement or unthreading of screw 64 from receiver 102. In some embodiments, driver 12 is manipulated to deliver one or more bone fasteners 100 to a surgical site including vertebrae.

Sensor array 302 receives signals from navigation component 300 to provide a three-dimensional spatial position and/or a trajectory of the assembly of driver 12/bone fastener 100, which may be disposed with end effector 200, relative to vertebrae and/or components of spinal implant system 10 for display on monitor 310. Wheel 84 is manipulated for rotation such that inner sleeve 56 and screw 64 rotates relative to outer sleeve 14, and thread form 89 disengages the thread forms of arms 104, 106. Screw 64 axially translates through opening 105 from receiver 102 to unthread driver 12 from receiver 102 such that wheel 84 is disposed in the proximal position and provides visual indicia, including gap G1, of the non-locking configuration of screw 64 relative to bone fastener 100, as shown in FIGS. 3 and 4.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 17-21, spinal implant system 10, similar to the systems and methods described herein, includes a driver 412, similar to driver 12 described herein. Driver 412 can be employed with end effector 200 of robotic arm R to facilitate implant with robotic arm R, as described herein. Driver 412 is guided through end effector 200 for guide-wireless insertion of a spinal implant, such as, for example, bone fastener 100, as described herein.

Figure 21:
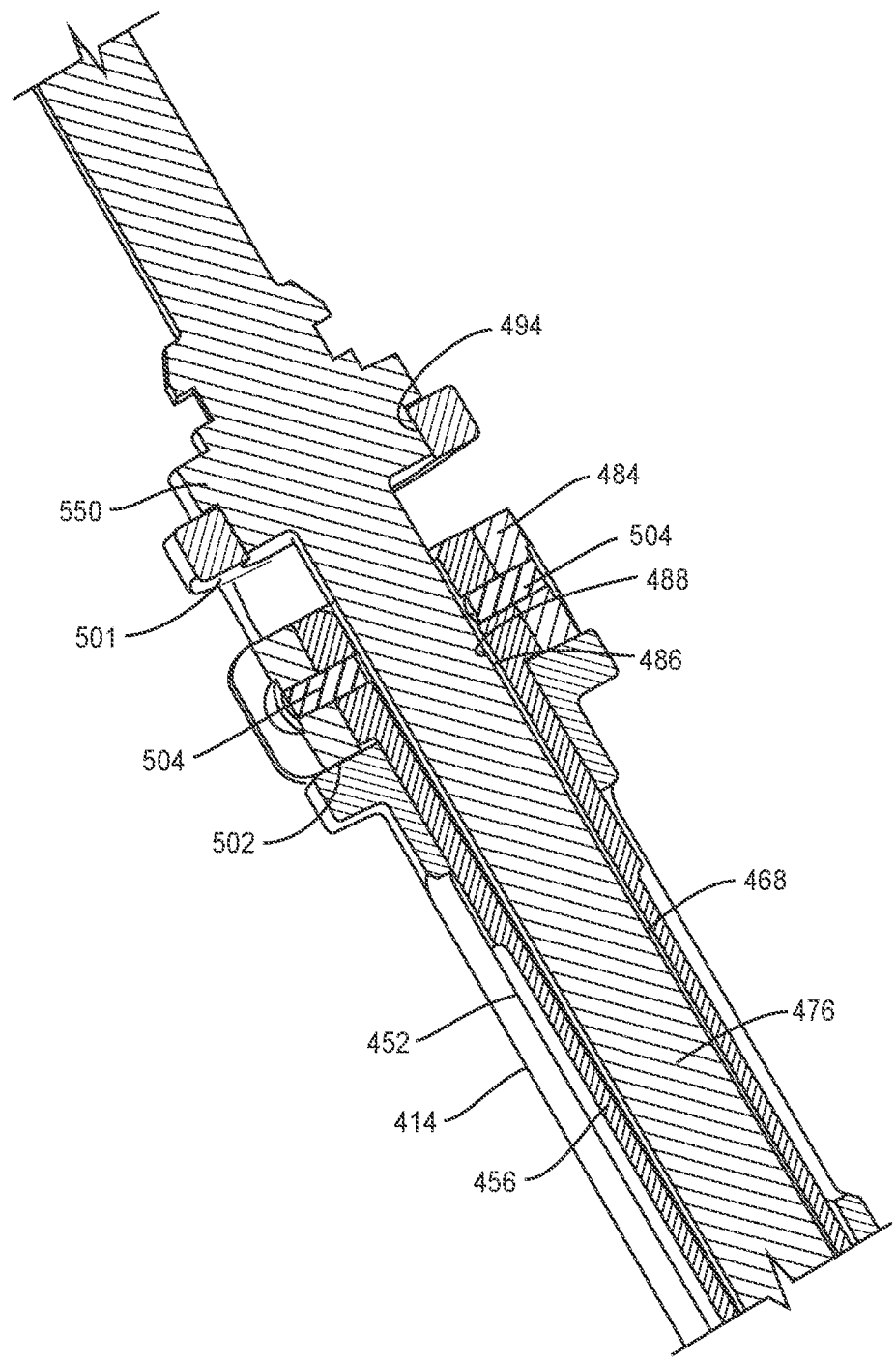
FIG. 21 is a break away view of the components shown in FIG. 20.

Driver 412 includes an outer tubular sleeve 414, similar to outer sleeve 14 described herein. Outer sleeve 414 extends between a proximal end 418 and a distal end 420. Outer sleeve 414 includes a surface 450 that defines an axial cavity 452. Cavity 452 is configured for disposal of an inner sleeve 456, similar to sleeve 56 described herein, and an inner shaft 476, similar to inner shaft 76 described herein. Outer sleeve 414 includes a collar body 416, similar to body 16 described herein, having a surface 480. Surface 480 defines a cavity 482. Body 416 includes bifurcated arms 492 disposed about cavity 482 to facilitate disposal and access to a thumb wheel 484 therein, similar to thumb wheel 84 described herein. Body 416 includes opening 494 disposed at end 418. Opening 494 includes a diameter configured to receive inner sleeve 456 to facilitate translation of inner sleeve 456 relative to outer sleeve 14 during assembly, as described herein. Opening 494 is in communication with cavity 482 and in alignment with cavity 452 to facilitate insertion of inner sleeve 465 and inner shaft 476 into end 418, through wheel 484 and into cavity 452 for assembly, as described herein. Wheel 484 is configured to actuate rotation of inner sleeve 456 and a screw 464, similar to that described herein. Wheel 484 includes a surface 486 that defines a cavity 488. Cavity 488 is configured for disposal of a correspondingly shaped portion of inner sleeve 456, as shown in FIG. 21.

Figure 19:
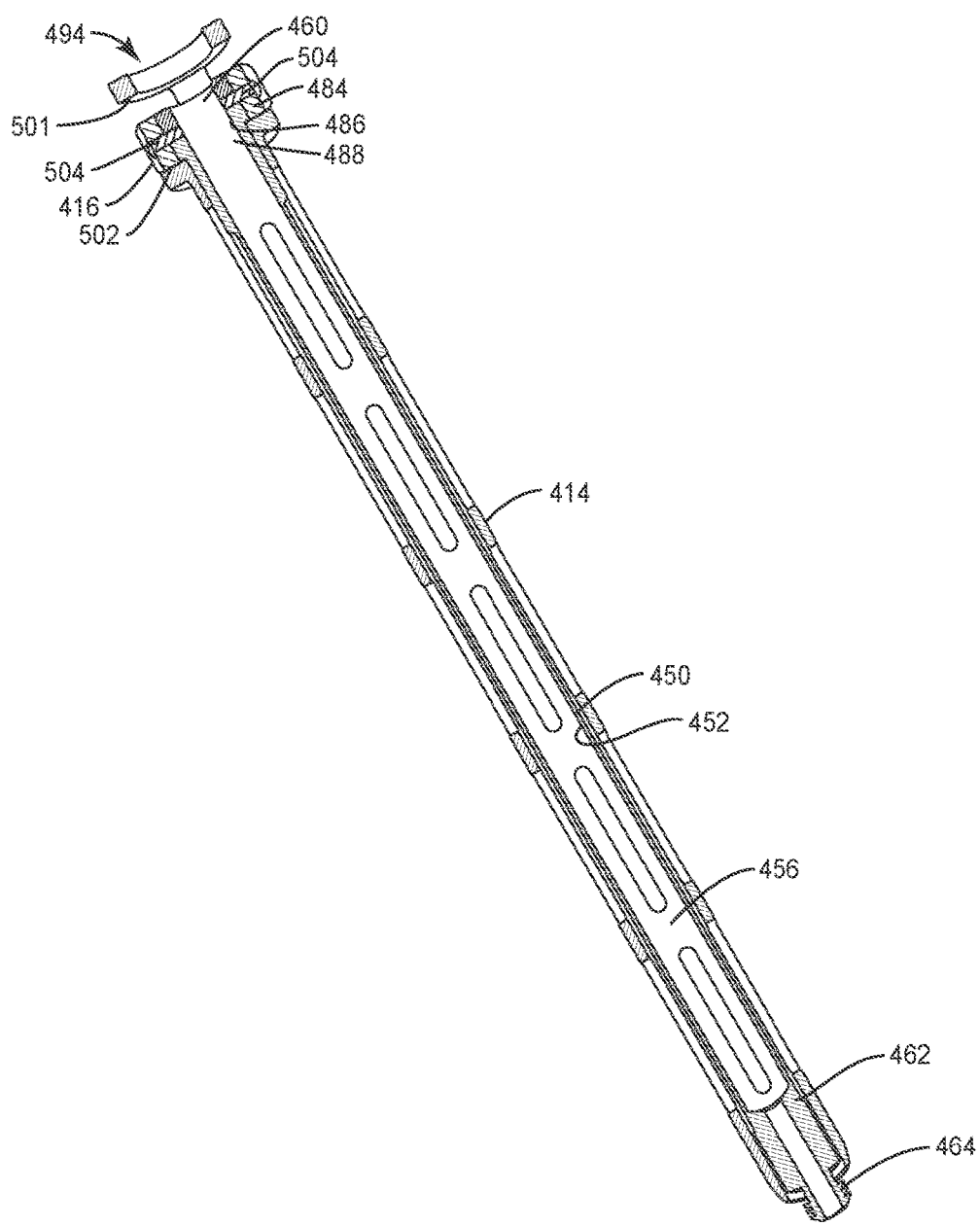
FIG. 19 is a cross section view of the components shown in FIG. 18.
Figure 20:
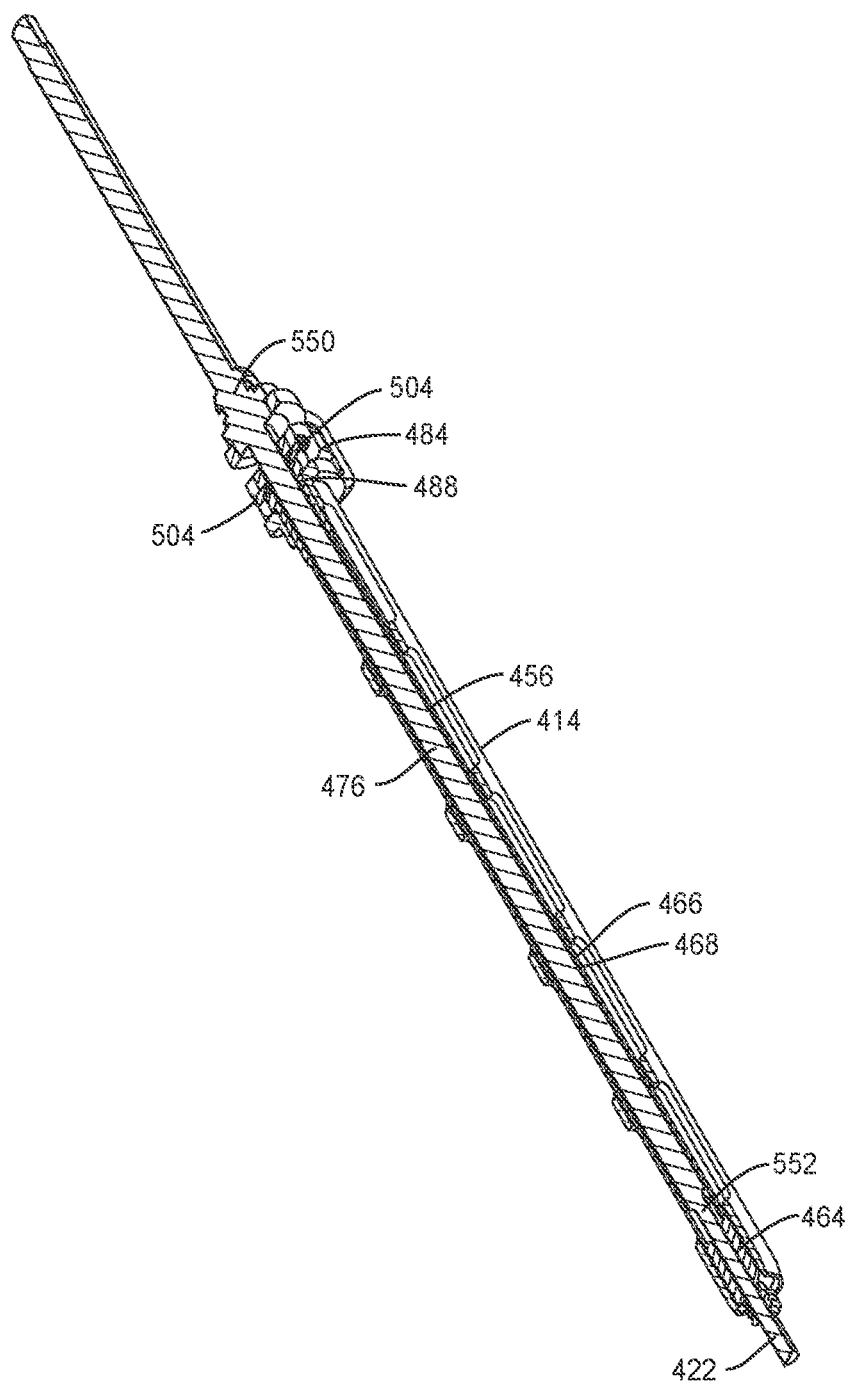
FIG. 20 is a cross section view of the components shown in FIG. 17.

Inner sleeve 456 extends between an end 460 and an end 462. End 460 is engageable with wheel 484. Wheel 484 actuates rotation of inner sleeve 456 and screw 464, similar to that described herein. Inner sleeve 456 is fixed with wheel 484 by pins 504, as shown in FIGS. 19-21. Pins 504 are configured to fix wheel 484 relative to inner sleeve 456 to resist and/or prevent rotation of wheel 484 relative to inner sleeve 456 to facilitate simultaneous rotation of wheel 484, inner sleeve 456 and screw 464.

Inner sleeve 456 includes an inner surface 466. Surface 466 defines an axial channel 468 configured for moveable disposal of inner shaft 476, as described herein. End 462 of inner sleeve 456 includes screw 464 configured to pull and or draw bone fastener 100 into engagement with driver 412, similar to screw 64 described herein.

Wheel 484 is translatable within cavity 482 causing simultaneous axial movement of inner sleeve 456 and screw 464 relative to outer sleeve 414. Body 416 includes ends 501, 502 that define a range of axial translation of wheel 484 relative to outer sleeve 414. Wheel 484 is moveable relative to outer sleeve 414 between a proximal position and a distal position, as described herein. In the proximal position, wheel 484 provides visual indicia of a non-locking configuration of screw 464 relative to bone fastener 100, as described herein. In the distal position, wheel 484 provides visual indicia of a locking configuration of screw 464 relative to bone fastener 100, as described herein.

Inner shaft 476 extends between an end 550 and an end 552. Inner shaft 476 is disposable with channel 468. End 550 is fixed with outer sleeve 414 such that rotation of inner shaft 476 causes simultaneous rotation of outer sleeve 414. Inner shaft 476 is welded with outer sleeve 414. Inner shaft 476 is rotatable independently of inner sleeve 456 such that rotation of inner shaft 476 to engage bone fastener 100 is separate and apart from rotation of inner sleeve 456 and screw 464. End 552 of inner shaft 476 includes a drive 422, similar to drive 22 described herein.

Figure 18:
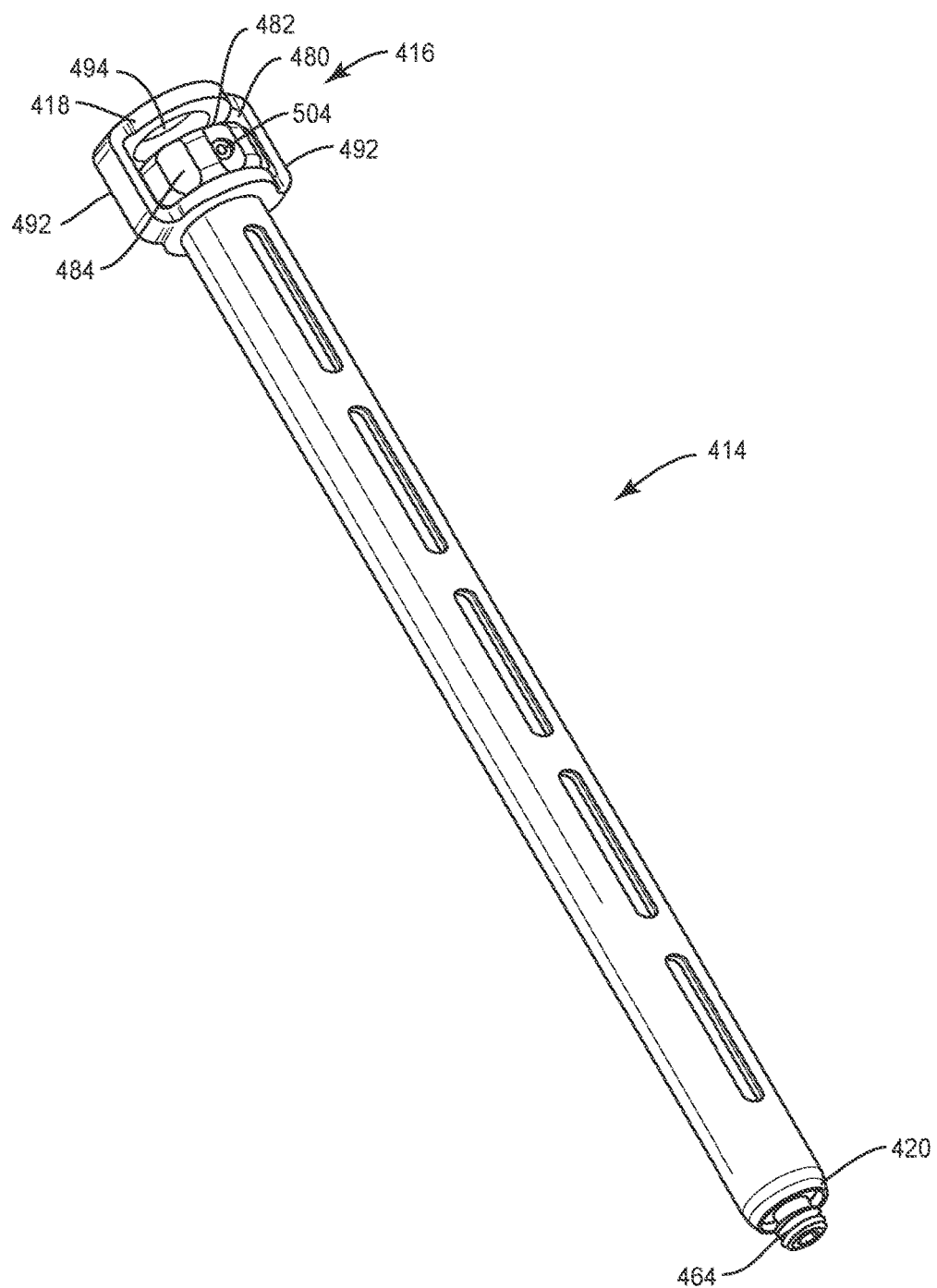
FIG. 18 is a perspective view of components of the system shown in FIG. 17.

For assembly of driver 412, wheel 484 is inserted laterally into cavity 482. Inner sleeve 456 is inserted from end 418 of outer sleeve 414, through opening 494 and through cavity 452, as shown in FIG. 18. Pins 504 are fixed with wheel 484 and inner sleeve 456, such as, for example, by laser welding, as shown in FIG. 19. After connection of inner sleeve 456 with outer sleeve 414, inner shaft 476 is inserted from end 418, through opening 494 and, through cavity 488 to provisionally connect wheel 484 with outer sleeve 414, as shown in FIGS. 20 and 21. Inner shaft 476 is welded to outer sleeve 414. Inner shaft 476 is disposed with cavity 468 of inner sleeve 456. Inner sleeve 456 is rotatable relative to outer sleeve 414 and inner shaft 476. Inner shaft 476 and outer sleeve 414 simultaneously rotate relative to inner sleeve 456, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   an outer sleeve including an inner surface that defines a cavity;
   an inner shaft permanently fixed with the outer sleeve and extending within the cavity, the inner shaft including a tip engageable with a first mating surface of a bone fastener; and
   an inner sleeve defining a passageway, the inner shaft being disposed in the passageway, the inner sleeve being rotatable relative to the outer sleeve and including an outer surface connectable with a second mating surface of the bone fastener.

2. A surgical instrument as recited in claim 1, wherein the inner sleeve is disposed between the inner shaft and the outer sleeve within the cavity in a relative coaxial orientation.

3. A surgical instrument as recited in claim 1, wherein the tip is a distal tip of the inner shaft and the first mating surface includes a drive socket of a bone fastener shaft.

4. A surgical instrument as recited in claim 1, further comprising a rotatable actuator connected with the inner sleeve.

5. A surgical instrument as recited in claim 4, wherein the rotatable actuator includes a knurled wheel including an inner surface engageable with the inner sleeve for rotation therewith.

6. A surgical instrument as recited in claim 1, wherein the outer surface is threaded and connectable with the second mating surface.

7. A surgical instrument as recited in claim 1, wherein the inner sleeve is axially translatable relative to the outer sleeve.

8. A surgical instrument as recited in claim 1, wherein the inner sleeve is axially translatable relative to the outer sleeve between a non-locking configuration and a locking configuration with the second mating surface.

9. A surgical instrument as recited in claim 1, further comprising an actuator connected with the inner sleeve and including visual indicia of engagement of the outer surface with the second mating surface.

10. A surgical instrument as recited in claim 9, wherein the actuator is axially translatable relative to the outer sleeve to provide visual indicia of a non-locking configuration and a locking configuration.

11. A surgical instrument as recited in claim 9, wherein the visual indicia includes the actuator disposed in a proximal position relative to the outer sleeve to provide visual indicia of a non-locking configuration and in a distal position relative to the outer sleeve to provide visual indicia of a locking configuration.

12. A surgical instrument as recited in claim 1, further comprising an actuator fixed with the inner sleeve in rotation and axial translation.

13. A surgical instrument as recited in claim 12, wherein the inner sleeve and the actuator are connected via at least one pin.

14. A surgical instrument as recited in claim 12, wherein the inner sleeve and the actuator are engageable in a snap-fit assembly.

15. A surgical instrument as recited in claim 12, wherein the inner surface of the actuator includes a wall defining a groove, and further comprising a band that is expandable within the groove, the inner sleeve being manually engageable with the band to connect the inner sleeve and the actuator.

16. A surgical instrument as recited in claim 12, wherein the inner surface of the actuator includes a wall defining a groove, and further comprising a circumferential ring that defines a gap and is expandable within the groove between a capture orientation and an expanded orientation.

17. A surgical instrument as recited in claim 1, wherein the passageway is coaxial with the cavity.

18. A surgical instrument comprising:
an outer sleeve including an inner surface that defines a cavity;
an inner shaft fixed with the outer sleeve and extending within the cavity, the inner shaft including a tip engageable with a first mating surface of a bone fastener;
an inner sleeve disposed between the inner shaft and the outer sleeve, the inner sleeve being rotatable relative to the outer sleeve and including an outer surface connectable with a second mating surface of the bone fastener; and
an actuator connected with the inner sleeve and including visual indicia of engagement of the outer surface with the second mating surface,
wherein the actuator is axially translatable relative to the outer sleeve to provide visual indicia of a non-locking configuration and a locking configuration.

19. A surgical instrument comprising:
an outer sleeve including an inner surface that defines a cavity;
an inner shaft fixed with the outer sleeve and extending within the cavity, the inner shaft including a tip engageable with a first mating surface of a bone fastener;
an inner sleeve disposed between the inner shaft and the outer sleeve, the inner sleeve being rotatable relative to the outer sleeve and including an outer surface connectable with a second mating surface of the bone fastener; and
an actuator fixed with the inner sleeve in rotation and axial translation.

* * * * *